(12) United States Patent
Park et al.

(10) Patent No.: US 10,494,601 B2
(45) Date of Patent: *Dec. 3, 2019

(54) METHOD FOR INDUCING THREE-DIMENSIONAL OSTEOGENIC DIFFERENTIATION OF STEM CELLS USING HYDROGEL

(71) Applicant: CEFO CO., LTD, Seoul (KR)

(72) Inventors: Hyun Sook Park, Seoul (KR); Sun Ray Lee, Seoul (KR); Ji Won Yang, Seoul (KR); Seol Chu, Suwon-si Gyeonggi-do (KR); Hyun Jung Mo, Anyang-si (KR)

(73) Assignee: CEFO CO., LTD, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/512,455

(22) PCT Filed: Sep. 15, 2015

(86) PCT No.: PCT/KR2015/009658
§ 371 (c)(1),
(2) Date: Mar. 17, 2017

(87) PCT Pub. No.: WO2016/043488
PCT Pub. Date: Mar. 24, 2016

(65) Prior Publication Data
US 2017/0283768 A1    Oct. 5, 2017

(30) Foreign Application Priority Data

Sep. 19, 2014   (KR) .................. 10-2014-0125316

(51) Int. Cl.
| | | |
|---|---|---|
| *C12N 5/00* | (2006.01) | |
| *C12M 1/12* | (2006.01) | |
| *C12N 5/0775* | (2010.01) | |
| *C12M 3/00* | (2006.01) | |
| *C12N 5/073* | (2010.01) | |

(52) U.S. Cl.
CPC ............. *C12N 5/0068* (2013.01); *C12M 3/00* (2013.01); *C12M 25/14* (2013.01); *C12N 5/0603* (2013.01); *C12N 5/0663* (2013.01); *C12N 5/0667* (2013.01); *C12N 5/0668* (2013.01); *C12N 5/00* (2013.01); *C12N 2513/00* (2013.01); *C12N 2533/30* (2013.01); *C12N 2537/10* (2013.01)

(58) Field of Classification Search
CPC ...... C12N 5/0068; C12N 5/0062; C12N 5/00; C12N 2513/00; C12N 2523/30; C12M 25/00
See application file for complete search history.

(56) References Cited

U.S. PATENT DOCUMENTS

2014/0206022 A1    7/2014   Nuti et al.

FOREIGN PATENT DOCUMENTS

| JP | 2009-542230 A | 12/2009 |
|---|---|---|
| JP | 2016013070 A | 1/2016 |
| JP | 2017526378 A | 9/2017 |
| KR | 10-2013-0091818 A | 8/2013 |
| WO | 2010062911 A2 | 6/2010 |

OTHER PUBLICATIONS

Hesse et al. Collagen Type I Hydreogel Allows Migration, Proliferation and Osteogenic Differentiation of Rat Bone Marrow Stromal Cells; vol. 94, No. 2, pp. 442-449. (Year: 2010).*
Forgacs et al. Assembly of Collagen Matrices as a Phase Transition Revealed by Structural and Rheologic Studies; Biophysics Journal, vol. 84, pp. 1272-1280. (Year: 2003).*
Anonymous. Stem Cell Basics IV, NIH, downloaded from https://stemcells.nih.gov/info/basics/4htm on Jun. 18, 2018. (Year: 2016).*
Myers et al. Three Dimensional Cultures of Normal and Malignant Human Breast Epithelial Cells to Achieve in Vivo-Like Architecture and Function; Cell Biology: A Laboratory Handbook, 3rd. Ed.,vol. 1, Chapter 17, p. 141, (Year: 2006).*
Allen et al. Type I Collagen, Fibrin and Puramatrix Matrices Provide Permissive Environments for Human Endothelial and Mesenchymal Progenitor Cells to Form Neovascular Networks; Journal of Tissue Engineering and Regenerative Medicine, vol. 5, No. 4, pp. 1-18. (Year: 2011).*
Kim et al. Synthesis and Characterization of Injectable Poly(N-Isopropylacrylamide-Co-Acrylic Acid) Hydrogels With Proteolytically Degradable Cross-Links; Biomacromolecules, vol. 4, pp. 1214-1223. (Year: 2003).*
Park et al. Multi-Lineage Differentiation of HMSCS Encapsulated in Thermo-Reversible Hydrogel Using a Co-Culture System With Differentiated Cells; Biomaterials, vol. 31, pp. 7275-7287. (Year: 2010).*
Jah, Amit K. et al., Controlling osteogenic stem cell differentiation via soft bioinspired hydrogels, PLoS One, Jun. 2014, p. 1-11, vol. 9.
Naito, Hiroshi et al., The effect of mesenchymal stem cell osteoblastic differentiation on the mechanical properties of engineered bone-like tissue, Tissue Engineering Part A, 2011, p. 2321-2329, vol. 17.

(Continued)

*Primary Examiner* — Julie Wu
*Assistant Examiner* — Paul C Martin
(74) *Attorney, Agent, or Firm* — Novick, Kim & Lee, PLLC; Jae Youn Kim

(57) ABSTRACT

The present invention relates to a method for inducing osteogenic differentiation of mesenchymal stem cells and, more particularly, to a short-time osteogenic differentiation method of culturing cells using a porous membrane and a biodegradable synthetic biogel, whereby the cells do not contact a cell culture container. The present invention can significantly shorten the induction period of osteogenic differentiation, compared to the conventional osteogenic differentiation method, and has an effect of the cells being easily separable after differentiation as well.

4 Claims, 6 Drawing Sheets

(56) References Cited

OTHER PUBLICATIONS

Nuttelman, Charles R. et al., In vitro osteogenic differentiation of human mesenchymal stem cells photoencapsulated in PEG hydrogels, Journal of Biomedical Materials Research Part A, 2004, p. 773-782, vol. 68A.

Huaping Tan et al., Injectable, Biodegradable Hydrogels for Tissue Engineering Applications, Materials, Mar. 10, 2010, pp. 1746-1767.

Masuda et al., A novel two-step method for the formation of tissue-engineered cartilage by mature bovine chondrocytes: the alginate-recovered-chondrocyte (ARC) method, Jan. 17, 2002, pp. 139-148.

* cited by examiner

METHOD FOR INDUCING THREE-DIMENSIONAL OSTEOGENIC DIFFERENTIATION OF STEM CELLS USING HYDROGEL

TECHNICAL FIELD

The present disclosure relates to a method for osteogenic differentiation on a synthetic bio-gel in a short time in the osteogenic differentiation induction of mesenchymal stem cells.

BACKGROUND ART

Due to the recent developments of tissue engineering and regenerative medicine, methods capable of treating damaged tissues and organs are being developed in a different manner from the conventional methods, and the cell therapy by mesenchymal stem cells is receiving most attention. Stem cells refer to cells that can proliferate indefinitely in an undifferentiated state as well as differentiating to have a specialized function and shape under specific environments and conditions. Examples of stem cells are: embryonic stem cells derived from human embryos; and adult stem cells, such as bone marrow cells that constantly generate blood cells. Embryonic stem cells can differentiate into all the cells and tissues constituting the human body, but the use thereof is limited for ethical reasons. Adult stem cells, on the other hand, are extracted from the umbilical cord blood or the bone marrow and blood of fully grown adults, enable the differentiation into specific tissues and organs after in vivo transplantation, and have the differentiation flexibility to transdifferentiate into cells of other tissues different from characteristics of original cells. Adult cells are widely used in tissue engineering without ethical limitations. In recent years, various attempts and early clinical trials are on the way in the medical field for the regeneration and replacement of tissues or organs of patients by growing stem cells and then differentiating the stem cells into specific cells. Mesenchymal stem cells are one type of adult stem cells present in various organs or blood of the body after the development and are a cell source that is easy to maintain and has no ethical problems. The mesenchymal stem cells are currently the most notable stem cell in the regenerative medicine field, but have a drawback in that the mesenchymal stem cells have limits in the in vitro subculture and differentiation potency compared with embryonic stem cells.

Studies on humans and animals have already confirmed that bone marrow-derived stem cells out of adult stem cells differentiate into osteogenic cells (Friedenstein A. J. et al., Transplantation., 6:230-247, 1968), and recent studies have progressed methods for culturing stem cells isolated from the bone marrow to differentiate the stem cells into osteoblasts, and there is an increasing possibility of clinical application using the methods (Ohgushi H. et al., J. Biomed Mater Res., 48:913-927, 1999). Recently, methods for differentiation into osteocytes from mesenchymal stem cells have dominantly been studied.

On the other hand, methods for the culture and differentiation of cells in a two-dimensional well plate are currently most widely used in the differentiation in stem cells. However, there are recent paper reports that two-dimensional (monolayer) cell culture lowers cell functions and significantly changes morphology compared with three-dimensional cell culture (Proc. Natl. Acad. Sci. USA, 100: 1943-1948, 2003; Cell, 111: 923-925, 2002; Cancer Cell 2: 205-216, 2002). The cell culture and differentiation in a manner of adversely affecting the state of cells as described above causes difficulty in differentiation and takes a long time. In order to overcome the drawbacks of such cell culture, Korean Patent No. 10-0733914 discloses a three-dimensional microcellular culture system characterized in that cells are present in a three-dimensional gel, but the gel needs to be dissolved in order to separate the cells present in the gel after the culture or differentiation of stem cells, causing severe cell damage.

DETAILED DESCRIPTION OF THE INVENTION

Technical Problem

The osteogenic differentiation induction in the conventional two-dimensional cell culture container has drawbacks in that only a portion of the stem cell is in contact with the medium, and thus, the inflow of nutrients, inductive ingredients, and air necessary for differentiation is not easy, thereby making the differentiation harder and causing the differentiation period to be longer, such as three to five weeks. A conventional three-dimensional culture method in which the cells are cultured inside a gel has a drawback in that cells cannot be separated. Accordingly, there is a need to develop a three-dimensional cell culture system that facilitates the separation and use of differentiated cells after osteogenic differentiation of stem cells.

Technical Solution

Therefore, in order to increase the contact surface area of cells with the medium to promote osteogenic differentiation while easily separating the cells, an aspect of the present disclosure is to provide a method in which cells exist inside a cell culture container in a non-contact manner and are in contact with the medium in all directions to promote osteogenic differentiation, thereby shortening the period for osteogenic differentiation.

Advantageous Effects

In cases where the osteogenic differentiation of stem cells is performed using the method for inducing osteogenic differentiation of stem cells of the present disclosure, the stem cells can be in contact with the medium with a wider surface area, thereby promoting the osteogenic differentiation induction of stem cells, thus remarkably shortening the period for osteogenic differentiation induction compared with the conventional method for osteogenic differentiation; and although the cells adhere to internal and external surfaces of the hydrogel, a gel-phase hydrogel is changed into a sol phase at a temperature below the cell culture temperature, 37° C., and thus, the cells can be easily separated even after differentiation.

BEST MODE FOR CARRYING OUT THE INVENTION

Figure 1:
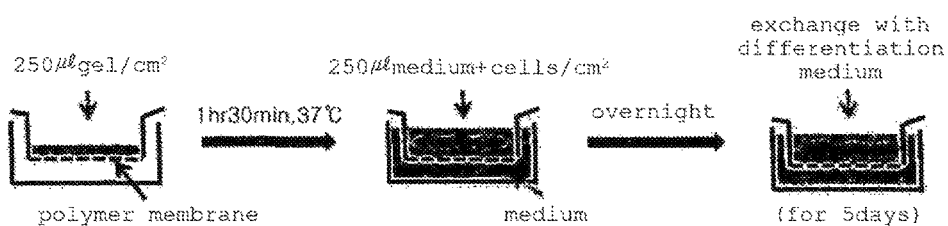
FIG. 1 is a schematic diagram showing a method for the differentiation of stem cells in a three-dimensional state according to the present disclosure.

Hereinafter, the present disclosure will be described in detail with reference to the following examples. However, the present disclosure may be realized in various different forms, and therefore is not limited to embodiments to be described herein.

In accordance with an aspect of the present disclosure, there is provided a method for inducing osteogenic differentiation of stem cells in a cell culture container inside which a porous membrane having one surface coated with a hydrogel is placed in a non-contact manner.

In an embodiment, the present disclosure may induce the osteogenic differentiation of stem cells, by including:
placing a porous membrane inside a cell culture container in a non-contact manner;
applying a hydrogel solution on one surface of the porous membrane to coat a hydrogel thereon through a sol-gel phase transition;
seeding stem cells on the coated hydrogel; and
culturing the stem cells in an osteogenic differentiation inducing medium.

In an embodiment, the method may further include a step of, before the culturing of stem cells in an osteogenic differentiation inducing medium after the seeding of stem cells, culturing the stem cells in an osteogenic differentiation pre-treatment medium for 10-24 hours. The pre-treatment medium may have a glucose concentration of 1.5 g/l or less.

In an embodiment, the porous membrane may be placed in parallel with the bottom of the cell culture container in a non-contact manner. The order of the coating of the hydrogel on the porous membrane and the placing of the porous membrane inside the cell culture container in a non-contact manner is not particularly limited. In such a case, the porous membrane may be disposed above the bottom of the cell culture container in a non-contact manner and then the hydrogel may be coated thereon, or the hydrogel may be coated on the porous membrane in advance and then the coated porous membrane may be disposed inside the cell container in a non-contact manner.

The cell culture container of the present disclosure generally refers to a dish or well plate used for cell culture, and the cell culture container is not particularly limited as long as it is used for cell culture and can introduce a porous membrane to the container bottom in a non-contact manner.

In an embodiment, in cases where cells are non-horizontally cultured inside the cell culture container to induce the osteogenic differentiation of stem cells, a hydrogel solution may be applied on one surface of the porous membrane, the cells may be allowed to adhere to the hydrogel, and then the resulting membrane may be placed inside the cell culture container in a non-contact manner to induce the osteogenic differentiation.

In an embodiment, the stem cells may be cultured in osteogenic differentiation inducing medium for 3-7 days.

In an embodiment, the medium flows in between the porous membrane and the cell culture container to increase the contact surface area between the stem cells and the medium, thereby shortening the period for osteogenic differentiation induction. The porous membrane and the hydrogel of the present disclosure allow the permeation of air and medium, and the medium flow in to fill a space between the porous membrane and the cell culture container, which is generated by disposing the porous membrane and the cell culture container in a non-contact manner, so that the medium and the air flow into even the adhering portion of the cells, and thus, the stem cells are in contact with the medium and air with a wider surface area, thereby shortening the time for osteogenic differentiation induction. For example, the existing osteogenic differentiation method takes three to five weeks, but the osteogenic differentiation by the method of the present disclosure occurs within 3-7 days.

The cell culture container of the present disclosure generally refers to a dish or well plate used for cell culture, and the cell culture container is not particularly limited as long as it is used for cell culture and can introduce a porous membrane to the container in a non-contact manner.

In an embodiment, the sol-gel phase transition of the hydrogel solution (hydrosol) into the hydrogel may be performed at 37° C. for 1 to 2 hours.

In an embodiment, the hydrogel may include 1-40% hydrogels, and more preferably 1-15% hydrogels. The differentiation of stem cells does not occur for 0% hydrogel, and the efficiency of osteogenic differentiation does not increase and thus is not meaningful for 40% or more hydrogels. However, the concentration of the hydrogel is not limited thereto.

In an embodiment, the 1-40% hydrogels may be coated on the porous membrane at 200-300 µl/cm$^2$, and the thickness of the hydrogels formed through the sol-gel phase transition may be 1-4 mm.

In an embodiment, the viscosity at 37° C. of the hydrogel may be 1.E+00 to 1.E+06 ($10^0$ to $10^6$) mPa·s depending on the concentration (%) of the hydrogel. In the hydrogel having a pore size out of the range, the adhesion or differentiation of stem cells may be difficult. The hydrogel of the present disclosure is in a gel phase at a cell culture temperature, 37° C., and thus the cells are cultured inside and outside the gel. The hydrogel of the present disclosure is changed into a sol phase at a temperature lower than the cell culture temperature, thereby facilitating the separation of cells after cell differentiation.

In an embodiment, the porous membrane may have a pore size of 0.1-8 µm, but the pore size is not limited as long as the pore size is such that medium and air can pass through the porous membrane but the hydrogel cannot pass through the porous membrane.

In an embodiment, the stem cells may be umbilical cord mesenchymal stem cells, adipose-derived mesenchymal stem cells, embryonic stem cell-derived mesenchymal stem cells, periodontal ligament cells, or bone marrow-derived mesenchymal stem cells. The origins of the stem cells are not particularly limited, and examples thereof may be cells derived from human, monkey, pig, horse, cow, sheep, dog, cat, mouse, or rabbit. The stem cells are preferably human-derived stem cells, but are not limited thereto.

As used herein, the term "porous membrane" or "polymer membrane" refers to a porous membrane, a permeable membrane, or film type material through which medium or air passes but the hydrogel fails to pass. Any porous structure through which the cell culture medium and the air pass is not particularly limited.

As used herein, the term "hydrogel" refers to a material wherein a liquid, containing water as a dispersion medium, is solidified through a sol-gel phase transition to lose fluidity and form a porous structure. Any hydrogel suitable for cell adhesion and culture is not particularly limited, and in one embodiment of the present disclosure, a biodegradable synthetic bio-gel was used.

As used herein, the term "stem cells" refers to undifferentiated cells having self-renewal and differentiation potency. Stem cells include sub-groups of pluripotent stem cells, multipotent stem cells, and unipotent stem cells, according to their differentiation capacity. The pluripotent stem cells mean cells that have the potency to differentiate into all tissues or cells constituting a living organism, and the multipotent stem cells means cells that do not have potency to differentiate into all kinds but into plural kinds of tissues or cells. Unipotent stem cells mean cells that have the potency to differentiate into a particular tissue or cell. The pluripotent stem cells may include embryonic stem cells (ES cells), embryonic germ cells (EG cells), induced pluripotent stem cells (iPS cells), etc. The multipotent stem cells may include adult stem cells, such as mesenchymal stem cells (derived from fat, bone marrow, umbilical cord blood, or umbilical cord, etc.), hematopoietic stem cells (derived from bone marrow or peripheral blood), neural stem cells, germ stem cells, etc. The unipotent stem cells may include committed stem cells for hepatocytes, which are usually quiescent with low self-renewal capacity, but vigorously differentiate into hepatocytes under certain conditions.

In accordance with an aspect of the present disclosure, there is provided an apparatus for the differentiation of stem cells, the system including:

a cell culture container; and a porous membrane configured to have one surface to which a hydrogel is attached, cells being to adhere to the hydrogel, wherein the hydrogel-attached porous membrane is disposed inside the cell culture container in a non-contact manner.

In an embodiment, the porous membrane and the hydrogel may allow the permeation of air and medium.

Mode for Carrying Out the Invention

The present disclosure will be described in more detail through the following examples. However, the following examples are provided merely to illustrate the present disclosure and not to restrict the scope of the present disclosure.

EXAMPLE

Example 1

Stem Cell Differentiation Method in Three-Dimensional State

In order to promote the differentiation of stem cells, the trial for three-dimensional differentiation was performed. To this end, a polymer membrane with a thickness of 0.4-1 μm (Corning, USA) was provided so as to be horizontal to the bottom of a cell culture dish or well in a non-contact manner. A biodegradable synthetic bio-gel (BASF, Germany) was dissolved in sterilized tertiary distilled water to prepare gels with various concentrations (%). Then, 250 μl/cm$^2$ of the prepared biodegradable synthetic bio-gels were coated on the polymer membranes, and then solidified at 37° C. for 1 hour and 30 minutes, thereby manufacturing cell culture containers. The thickness of the biodegradable synthetic bio-gel after the sol-gel phase transition was at least 1 mm, and the average was 2.5 mm. The adipose-derived mesenchymal stem cells in CEFOgro ADMSC medium (CB-ADMSC-GM, CEFO, Korea), the bone marrow-derived mesenchymal stem cells in CEFOgro BMMSC medium (CB-BMMSC-GM, CEFO, Korea), the embryonic stem cell-derived mesenchymal stem cells in CEFOgro ESMSC medium (CB-ESMSC-GM, CEFO, Korea), the umbilical cord mesenchymal stem cells in CEFOgro UCMSC medium (CB-UCMSC-GM, CEFO, Korea), the periodontal ligament cells (PDL) in CEFOgro PDL medium (CB-PDL-GM, CEFO, Korea) were cultured in the $CO_2$ incubator at 37° C. for 3-4days. Thereafter, each type of stem cells was seeded on the bio-gel, and the osteogenic differentiation pre-treatment medium (CB-DM-Osteo-PT, CEFO, Korea) was added thereto, followed by culture in the $CO_2$ incubator at 37° C. for 18 hours. Thereafter, the medium was exchanged with osteogenic differentiation inducing medium (CB-DM-Osteo, CEFO, Korea), and then the osteogenic differentiation was induced in the $CO_2$ incubator at 37° C. for 5days (FIG. 1).

Comparative Example 1

Stem Cell Differentiation Method in Two-Dimensional State

Figure 2:
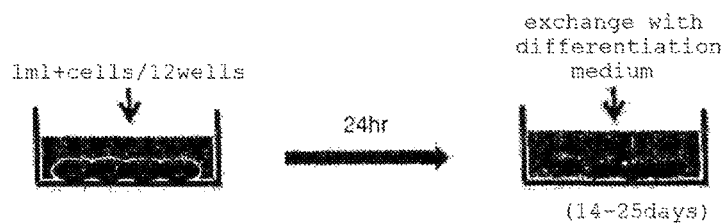
FIG. 2 is a schematic diagram showing a method for the differentiation of stem cells in a two-dimensional state using a culture dish according to the conventional art.

Stem cells were differentiated by a two-dimensional differentiation method, which is the conventional stem cell differentiation method. Specifically, the cells were seeded in the 12-well cell culture container (dish), and cultured in the pre-treatment medium (CB-DM-Osteo-PT, CEFO, Korea) for inducing osteogenic differentiation until the cell density reaches 85-90%. Thereafter, the medium was exchanged with the osteogenic differentiation inducing medium (CB-DM-Osteo, CEFO, Korea), followed by osteogenic differentiation induction for 14-21 days (FIG. 2).

Comparative Example 2

Stem Cell Differentiation Method in Three-Dimensional State Without Hydrogel

Figure 3:
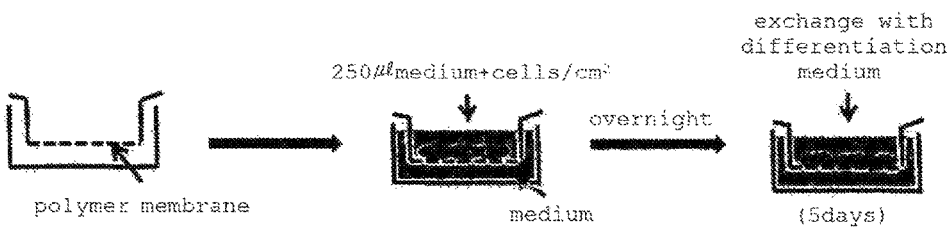
FIG. 3 is a schematic diagram showing a method for three-dimensional differentiation of stem cells using only a polymer membrane without a hydrogel.

In order to investigate the differentiation of stem cells when the biodegradable synthetic bio-gel on the polymer membrane in Example 1 is 0% (only polymer membrane is present), stem cells were seeded on the polymer membrane, and then cultured for 5 days like in Example 1 (FIG. 3).

Test Example 1

Figure 4:
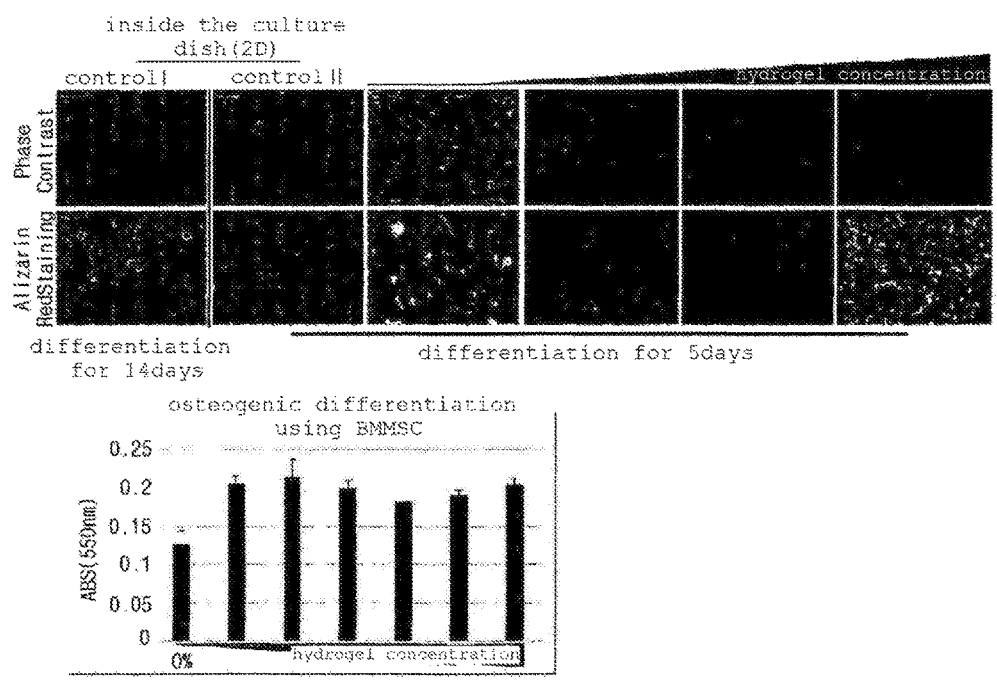
FIG. 4 confirms the osteogenic differentiation of bone marrow-derived mesenchymal stem cells, induced by the method of Comparative Example 1 (14 days: control 1, 5 days: control II), the method of Comparative Example 2 (lane 3, hydrogel concentration 0%), and the method of Example.

Verification on Osteogenic Differentiation of Bone Marrow-Derived Mesenchymal Stem Cells The bone marrow-derived mesenchymal stem cells undergoing osteogenic differentiation induced by the method of Comparative Example 1 for 14 days or 5 days, the bone marrow-derived stem cells undergoing osteogenic differentiation induced by the method of Comparative Example 2 (0% biodegradable synthetic bio-gel) for 5 days, and the bone marrow-derived stem cells undergoing osteogenic differentiation induced by the method of Example above (5%, 10%, or 15% biodegradable synthetic bio-gel) were visually observed for osteogenic differentiation through a phase contrast microscope. In addition, in order to investigate the osteogenically differentiated cells through Alizarin red staining, the cells were washed twice with PBS, fixed with 70% ethyl alcohol at room temperature for 10 minutes, and then washed twice with tertiary distilled water. Thereafter, the cells were treated with Sol I of Alizarin Red staining kit (CB-SK-Osteo), followed by reaction at room temperature for 30 minutes. Thereafter, the cells were cleanly washed three times with Sol II, and subjected to image analysis using an inverted microscope (LEICA, Germany). In addition, for digitization of the results, the cells were treated with Sol III after image synthesis to perform a reaction for 30 minutes, so that the stained reagent was completely dissolved. Then, 100 μl of the dissolved solution was taken, placed in a 96-well plate, and the absorbance was measured at 550 nm. As a result, the osteogenic differentiation was not attained when the osteogenic differentiation was induced by the method of Comparative Example 1 for 5 days and when the osteogenic differentiation was induced by the method of Comparative Example 2 for 5 days, but sufficient osteogenic differentiation was induced when the osteogenic differentiation was induced by the method of Example for 5 days. Especially, it could be seen that, with respect to the osteogenic differentiation by the method of Example above, the osteogenic differentiation occurred favorably in all the 1 to 30% hydrogels, and the most optimal osteogenic differentiation was shown at a concentration of 10% (FIG. 4).

Test Example 2

Figure 5:
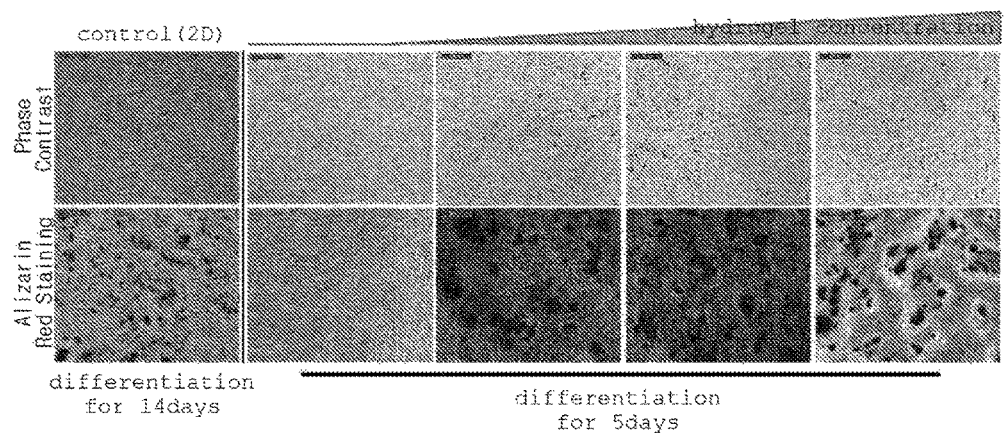
FIG. 5 confirms the osteogenic differentiation of bone marrow-derived mesenchymal stem cells, induced by the method of Comparative Example 1, the method of Comparative Example 2 (lane 2), and the method of Example.

Verification on Osteogenic Differentiation of Adipose-Derived Mesenchymal Stem Cells The adipose-derived mesenchymal stem cells undergoing osteogenic differentiation induced by the method of Comparative Example 1 for 14 days, the bone marrow-derived stem cells undergoing osteogenic differentiation induced by the method of Comparative Example 2 (0% biodegradable synthetic bio-gel) for 5 days, and the bone marrow-derived stem cells undergoing osteogenic differentiation induced by the method of Example above (5%, 10%, or 15% biodegradable synthetic bio-gel) were visually observed for osteogenic differentiation through a phase contrast microscope. In addition, in order to investigate the osteogenically differentiated cells through Alizarin red staining, the cells were washed twice with PBS, fixed with 70% ethyl alcohol at room temperature for 10 minutes, and then washed twice with tertiary distilled water. Thereafter, the cells were treated with Sol I of Alizarin Red staining kit (CB-SK-Osteo), followed by reaction at room temperature for 30 minutes. Thereafter, the cells were cleanly washed three times with Sol II, and subjected to image analysis using an inverted microscope (LEICA, Germany). As a result, it could be seen that the osteogenic differentiation never occurred when the osteogenic differentiation was induced by the method of Comparative Example 2 for 5 days, but when the osteogenic differentiation was induced by the method of Example for 5 days, the osteogenic differentiation was favorably attained in all the 1 to 30% biodegradable synthetic hydrogels, and the most optimal osteogenic differentiation was shown at a concentration of 5-10% (FIG. 5).

Test Example 3

Figure 6:
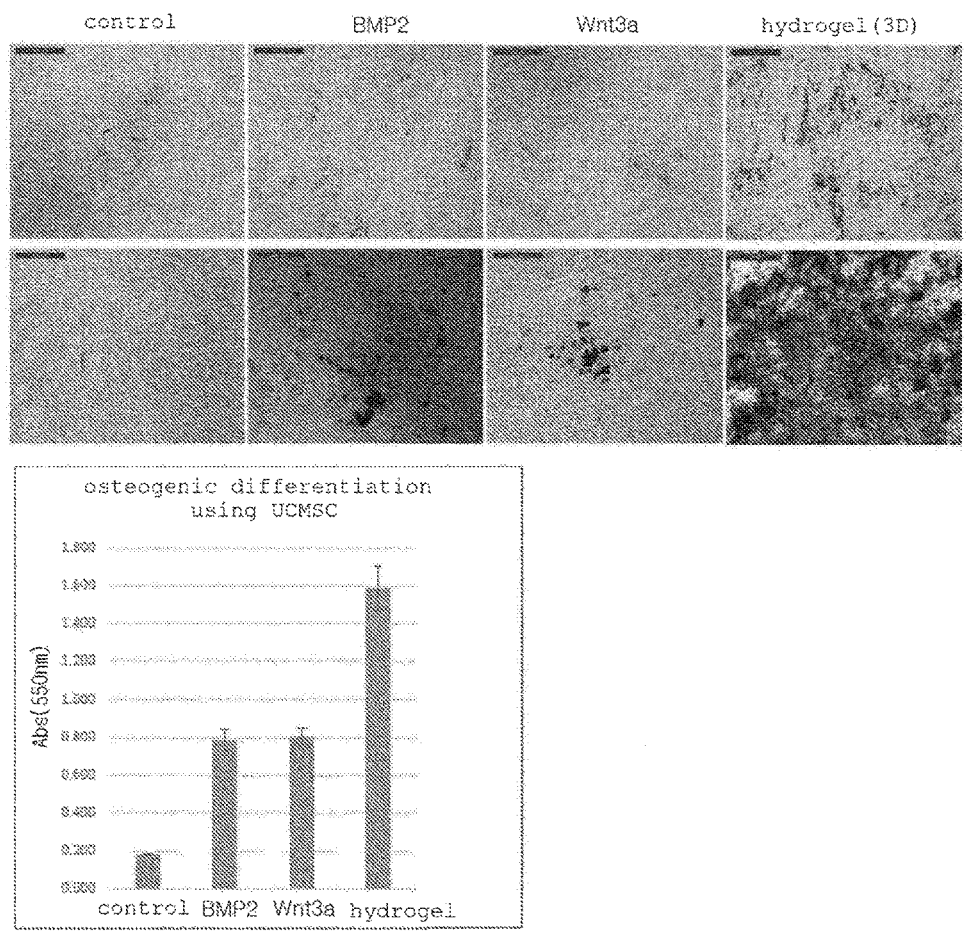
FIG. 6 confirms the degrees of osteogenic differentiation of umbilical cord mesenchymal stem cells, induced by the method of Comparative Example 2 (control), the method of Comparative Example 2+100 ng/ml BMP2or 20 ng/ml Wnt3a, and the method of Example.

Verification on Osteogenic Differentiation of Umbilical Cord Mesenchymal Stem Cells The umbilical cord mesenchymal stem cells undergoing osteogenic differentiation induced by the method of Comparative Example 2 for 5 days, the umbilical cord mesenchymal stem cells seeded by the method of Comparative Example 2, treated with 100 ng/ml bone morphogenic protein 2 (BMP 2, peprotech, israel) or 20 ng/ml Wnt3a (peprotech, israel), and then undergoing osteogenic differentiation induction for 5 days, the umbilical cord mesenchymal stem cells undergoing osteogenic differentiation induction by the method of Example above (10% biodegradable synthetic bio-gel) were visually observed for osteogenic differentiation through a phase contrast microscope. In addition, in order to investigate the osteogenically differentiated cells through Alizarin red staining, the cells were washed twice with PBS, fixed with 70% ethyl alcohol at room temperature for 10 minutes, and then washed twice with tertiary distilled water. Thereafter, the cells were treated with Sol I of Alizarin Red staining kit (CB-SK-Osteo), followed by reaction at room temperature for 30 minutes. Thereafter, the cells were cleanly washed three times with Sol I, and subjected to image analysis using an inverted microscope (LEICA, Germany). In addition, for digitization of the results, the cells were treated with Sol III after image synthesis to perform a reaction for 30 minutes, so that the stained reagent was completely dissolved. Then, 100 μl of the dissolved solution was taken, placed in a 96-well plate, and the absorbance was measured at 550 nm. As a result, the osteogenic efficiency was significantly excellent in the umbilical cord mesenchymal stem cells using the method of Example of the present disclosure rather than when the osteogenic differentiation was induced by the method of Comparative Example 2 for 5 days plus the treatment with BMP and Wnt3a known to promote osteogenic differentiation (FIG. 6).

Test Example 4

Figure 7:
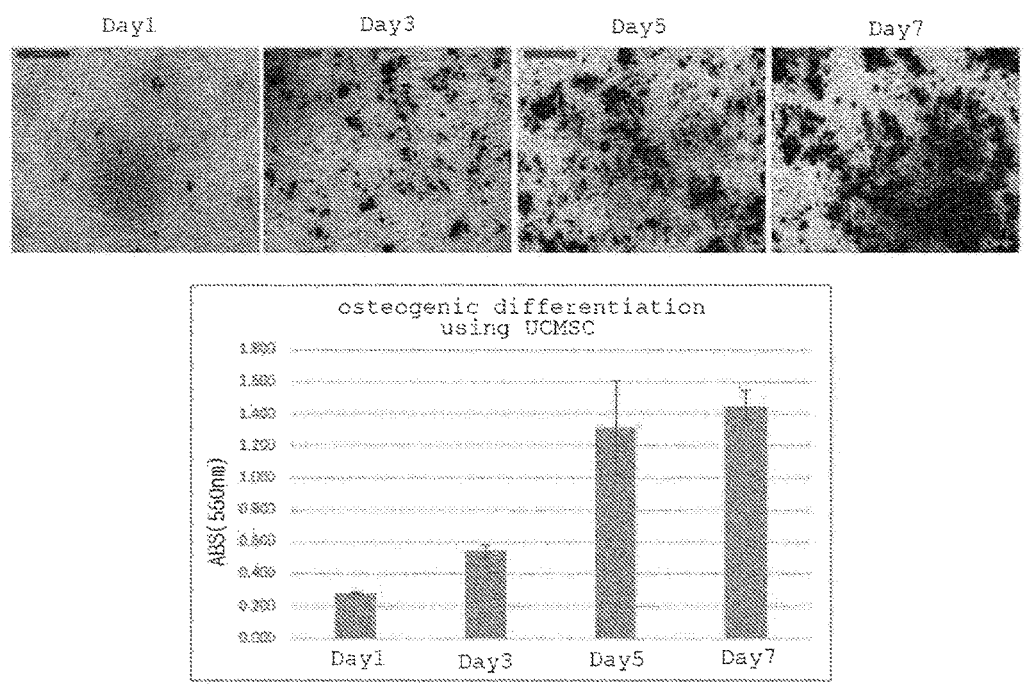
FIG. 7 confirms the degrees of osteogenic differentiation of umbilical cord mesenchymal stem cells, induced by the method of Example for 1 day, 3 days, 5 days, or 7 days.

Verification on Change Depending the Period for Osteogenic Differentiation of Umbilical Cord Mesenchymal Stem Cells The umbilical cord mesenchymal stem cells undergoing osteogenic differentiation for 1, 3, 5, or 7 days by the method of Example above (10% biodegradable synthetic bio-gel) were subjected to image analysis through Alizarin red staining. In addition, for digitization of the results, the absorbance was measured at 550 nm. As a result, the induction of osteogenic differentiation began from the 1st day of osteogenic differentiation induction, and the osteogenic differentiation was stronger as the period for osteogenic differentiation was longer. Especially, the umbilical cord mesenchymal stem cells, which have been known to undergo less osteogenic differentiation in the conventional two-dimensional method compared with the other types of mesenchymal stem cells, showed favorable osteogenic differentiation in the three-dimensional osteogenic differentiation method of Example of the present disclosure, like the other types of mesenchymal stem cells (FIG. 7).

Test Example 5

Verification on Osteogenic Differentiation of Various Types of Mesenchymal Stem Cells Bone marrow-derived mesenchymal stem cells, adipose-derived mesenchymal stem cells, umbilical cord mesenchymal stem cells, embryonic stem cell-derived mesenchymal stem cells, and periodontal ligament cell were allowed to undergo the induction of osteogenic differentiation by the method of Comparative Example 1 for 14 days, the method of Comparative Example 2 (0% biodegradable synthetic bio-gel) for 5 days, or the method of Example above (10% biodegradable synthetic bio-gel) for 5 days, and then the degree of osteogenic differentiation of each type of mesenchymal stem cells was investigated through Alizarin red staining.

Figure 8:
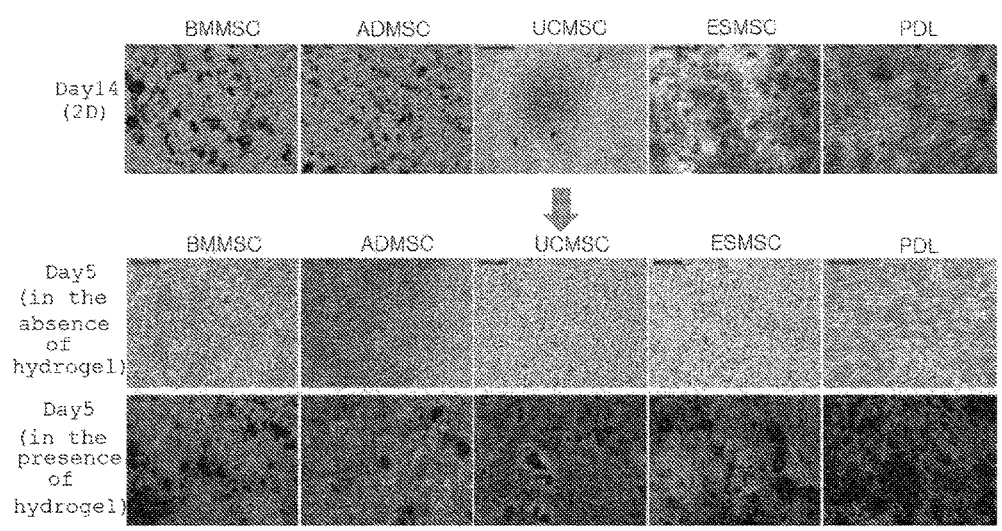
FIG. 8 shows the results of osteogenic differentiation induction of bone marrow-mesenchymal stem cells (BMMSC), adipose-derived mesenchymal stem cells (ADMSC), umbilical cord mesenchymal stem cells (UC-MSC), embryonic stem cell-derived mesenchymal stem cells (ESMSC), and periodontal ligament cells (PDL) by the method of Comparative Example 1, the method of Comparative Example 2 (without hydrogels), and the method of Example.

As a result, the osteogenic differentiation of the mesenchymal stem cells was not induced when the osteogenic differentiation was induced for 5 days by the method of Comparative Example 1 and the method of Comparative Example 2, but the osteogenic differentiation was favorably induced regardless of the origin of the mesenchymal stem cells when the osteogenic differentiation was three-dimensionally induced on the biodegradable synthetic bio-gel for 5 days (FIG. 8).

As described above, it was verified that the osteogenic differentiation of mesenchymal stem cells takes about 2-5 weeks by the conventional two-dimensional osteogenic differentiation method, but the osteogenic differentiation occurs within 3-7 days when using the three-dimensional osteogenic differentiation method of the present disclosure of placing the polymer membrane above the cell culture container in a non-contact manner, coating the hydrogel thereon, seeding the mesenchymal stem cells thereon, culturing the mesenchymal stem cells in the osteogenic differentiation pre-treatment medium, and treating the mesenchymal stem cells with the osteogenic differentiation inducing medium.

The invention claimed is:

1. A method for in vitro inducing osteogenic differentiation from mesenchymal stem cells for 3-7 days, the method comprising:
   preparing a cell culture container having an inside bottom surface;
   placing a porous membrane inside the cell culture container in a manner such that a space is formed between the bottom surface of the cell culture container and the porous membrane;
   applying a biodegradable synthetic bio-gel solution with a concentration of 5-15% on one surface of the porous membrane;
   solidifying the biodegradable synthetic bio-gel solution into a gel phase at a cell culture temperature, wherein a viscosity of a coated biodegradable synthetic bio-gel at the cell culture temperature is 1E+00 to 1E+06 ($10^0$ to $10^6$) mPa·s and a thickness of the coated biodegradable synthetic bio-gel is 1 mm to 4 mm;
   seeding the mesenchymal stem cells on the coated biodegradable synthetic bio-gel;
   culturing and differentiating the mesenchymal stem cells for osteogenesis in an osteogenic differentiation inducing medium for 3-7 days; and
   separating the differentiated cells by changing the biodegradable synthetic bio-gel into a sol phase at lower than the cell culture temperature.

2. The method of claim 1, wherein air and the medium permeate the porous membrane and the coated biodegradable synthetic bio-gel, and the medium flows into the formed space between the porous membrane and the cell culture container to increase a contact surface area between the mesenchymal stem cells and the medium, thereby shortening a period for osteogenic differentiation induction.

3. The method of claim 1, wherein the mesenchymal stem cells are umbilical cord mesenchymal stem cells, adipose-derived mesenchymal stem cells, embryonic stem cell-derived mesenchymal stem cells, periodontal ligament cells, or bone marrow-derived mesenchymal stem cells.

4. The method of claim 1, wherein the sol-gel phase transition is performed at 37° C. for 1 to 2 hours.

* * * * *